(12) United States Patent
Eckhardt et al.

(10) Patent No.: US 9,145,434 B2
(45) Date of Patent: Sep. 29, 2015

(54) CRYSTALLINE COMPLEX OF 1-CYANO-2-(4-CYCLOPROPYL-BENZYL)-4-(SS-D-GLUCOPYRANOS-1-YL)-BENZENE, METHODS FOR ITS PREPARATION AND THE USE THEREOF FOR PREPARING MEDICAMENTS

(71) Applicants: Matthias Eckhardt, Biberach an der Riss (DE); Tanja Butz, Merklingen (DE); Frank Himmelsbach, Mittelbiberach (DE); Hans-Juergen Martin, Biberach an der Riss (DE)

(72) Inventors: Matthias Eckhardt, Biberach an der Riss (DE); Tanja Butz, Merklingen (DE); Frank Himmelsbach, Mittelbiberach (DE); Hans-Juergen Martin, Biberach an der Riss (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 46 days.

(21) Appl. No.: 13/948,751

(22) Filed: Jul. 23, 2013

(65) Prior Publication Data

US 2014/0031540 A1     Jan. 30, 2014

(30) Foreign Application Priority Data

Jul. 26, 2012   (EP) .................................... 12177944

(51) Int. Cl.
| | |
|---|---|
| C07H 7/04 | (2006.01) |
| A61K 31/70 | (2006.01) |
| C07H 15/26 | (2006.01) |
| C07D 309/10 | (2006.01) |

(52) U.S. Cl.
CPC .............. *C07H 15/26* (2013.01); *C07D 309/10* (2013.01); *C07H 7/04* (2013.01)

(58) Field of Classification Search
None
See application file for complete search history.

(56) References Cited

U.S. PATENT DOCUMENTS

| | | | | |
|---|---|---|---|---|
| 7,745,414 B2 * | 6/2010 | Eckhardt et al. | ................ | 514/23 |
| 2014/0031540 A1 | 1/2014 | Eckhardt et al. | | |
| 2014/0303096 A1 | 10/2014 | Reiche et al. | | |

FOREIGN PATENT DOCUMENTS

| | | | |
|---|---|---|---|
| EP | 2048150 | A1 | 4/2009 |
| WO | 02083066 | A2 | 10/2002 |
| WO | 2007093610 | A1 | 8/2007 |
| WO | 2007128749 | A1 | 11/2007 |
| WO | 2008002824 | A1 | 1/2008 |
| WO | 2008116179 | A1 | 9/2008 |
| WO | 2010023594 | A1 | 3/2010 |
| WO | 2010048358 | A2 | 4/2010 |
| WO | 2014016381 | A1 | 1/2014 |

OTHER PUBLICATIONS

Deshpande et al., "A Practical Stereoselective Synthesis and Novel Cocrystallizations of an Amphiphatic SGLT-2 Inhibitor". Organic Process Research & Development, vol. 16, 2012, pp. 577-585.
International Search Report and Written Opinion of PCT/EP2013/065736 mailed Sep. 3, 2013.

* cited by examiner

Primary Examiner — Traviss C McIntosh, III
(74) Attorney, Agent, or Firm — Michael P. Morris

(57) ABSTRACT

The invention relates to a crystalline complex of 1-cyano-2-(4-cyclopropyl-benzyl)-4-(β-D-glucopyranos-1-yl)-benzene and a natural amino acid, to methods for the preparation thereof, as well as to uses thereof for preparing medicaments.

13 Claims, 2 Drawing Sheets

X-ray powder diffraction pattern of a representative batch of the crystalline complex of the compound A with L-proline (1:1)

DSC/TG diagram of a representative batch of the crystalline complex of the compound A with L-proline (1:1)

CRYSTALLINE COMPLEX OF 1-CYANO-2-(4-CYCLOPROPYL-BENZYL)-4-(SS-D-GLUCOPYRANOS-1-YL)-BENZENE, METHODS FOR ITS PREPARATION AND THE USE THEREOF FOR PREPARING MEDICAMENTS

The invention relates to a crystalline complex of 1-cyano-2-(4-cyclopropyl-benzyl)-4-(β-D-glucopyranos-1-yl)-benzene, to methods for the preparation thereof, as well as to the use thereof for preparing medicaments.

BACKGROUND OF THE INVENTION

The compound 1-cyano-2-(4-cyclopropyl-benzyl)-4-(β-D-glucopyranos-1-yl)-benzene (in the following referred to it as "compound A") is described in WO 2007/128749 and has the chemical structure according to formula A

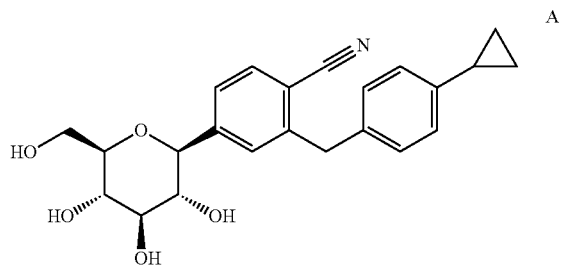 [SMILES: N#Cc1ccc([C@@H]2O[C@H](CO)[C@@H](O)[C@H](O)[C@H]2O)cc1Cc1ccc(C2CC2)cc1]

The compounds described therein have a valuable inhibitory effect on the sodium-dependent glucose cotransporter SGLT, particularly SGLT2. The method of manufacture of the compound A as described therein does not yield a crystalline form.

A certain pharmaceutical activity is of course the basic prerequisite to be fulfilled by a pharmaceutically active agent before same is approved as a medicament on the market. However, there are a variety of additional requirements a pharmaceutically active agent has to comply with. These requirements are based on various parameters which are connected with the nature of the active substance itself. Without being restrictive, examples of these parameters are the stability of the active agent under various environmental conditions, its stability during production of the pharmaceutical formulation and the stability of the active agent in the final medicament compositions. The pharmaceutically active substance used for preparing the pharmaceutical compositions should be as pure as possible and its stability in long-term storage must be guaranteed under various environmental conditions. This is essential to prevent the use of pharmaceutical compositions which contain, in addition to the actual active substance, breakdown products thereof, for example. In such cases the content of active substance in the medicament might be less than that specified.

Uniform distribution of the medicament in the formulation is a critical factor, particularly when the medicament has to be given in low doses. To ensure uniform distribution, the particle size of the active substance can be reduced to a suitable level, e.g. by grinding. Since breakdown of the pharmaceutically active substance as a side effect of the grinding (or micronising) has to be avoided as far as possible, in spite of the hard conditions required during the process, it is essential that the active substance should be highly stable throughout the grinding process. Only if the active substance is sufficiently stable during the grinding process it is possible to produce a homogeneous pharmaceutical formulation which always contains the specified amount of active substance in a reproducible manner.

Another problem which may arise in the grinding process for preparing the desired pharmaceutical formulation is the input of energy caused by this process and the stress on the surface of the crystals. This may in certain circumstances lead to polymorphous changes, to amorphization or to a change in the crystal lattice. Since the pharmaceutical quality of a pharmaceutical formulation requires that the active substance should always have the same crystalline morphology, the stability and properties of the crystalline active substance are subject to stringent requirements from this point of view as well.

The stability of a pharmaceutically active substance is also important in pharmaceutical compositions for determining the shelf life of the particular medicament; the shelf life is the length of time during which the medicament can be administered without any risk. High stability of a medicament in the abovementioned pharmaceutical compositions under various storage conditions is therefore an additional advantage for both the patient and the manufacturer.

The absorption of moisture reduces the content of pharmaceutically active substance as a result of the increased weight caused by the uptake of water. Pharmaceutical compositions with a tendency to absorb moisture have to be protected from moisture during storage, e.g. by the addition of suitable drying agents or by storing the drug in an environment where it is protected from moisture. Preferably, therefore, a pharmaceutically active substance should be at best slightly hygroscopic.

Furthermore, the availability of a well-defined crystalline form allows the purification of the drug substance by recrystallization.

Apart from the requirements indicated above, it should be generally borne in mind that any change to the solid state of a pharmaceutical composition which is capable of improving its physical and chemical stability gives a significant advantage over less stable forms of the same medicament.

The aim of the invention is thus to provide a new, stable crystalline form of the compound A which meets important requirements imposed on pharmaceutically active substances as those mentioned above.

OBJECT OF THE INVENTION

In a first aspect the present invention relates to a crystalline complex between one or more natural amino acids and 1-cyano-2-(4-cyclopropyl-benzyl)-4-(β-D-glucopyranos-1-yl)-benzene.

In the light of the pharmaceutical efficacy of the compound A and the advantageous physical chemical properties of the crystalline complex a second aspect of the present invention relates to a pharmaceutical composition or medicament comprising one or more crystalline complexes as defined hereinbefore and hereinafter.

A further aspect of the present invention relates to the crystalline complex for use as a medicament.

In a further aspect the present invention relates to a use of one or more crystalline complexes as defined hereinbefore or hereinafter for preparing a pharmaceutical composition which is suitable for the treatment or prevention of diseases or conditions which can be influenced by inhibiting sodium-dependent glucose cotransporter SGLT, preferably SGLT2.

In a further aspect the present invention relates to a use of one or more crystalline complexes as defined hereinbefore or hereinafter for preparing a pharmaceutical composition for inhibiting the sodium-dependent glucose cotransporter SGLT2.

In a further aspect the present invention relates to a method for making one or more crystalline complexes as defined hereinbefore and hereinafter, said method comprising the following steps:
a) preparing a solution of 1-cyano-2-(4-cyclopropyl-benzyl)-4-(β-D-glucopyranos-1-yl)-benzene and the one or more natural amino acids in a solvent or a mixture of solvents;
b) storing the solution to precipitate the crystalline complex out of solution;
c) removing the precipitate from the solution; and
d) drying the precipitate optionally until any excess of said solvent or mixture of solvents has been removed.

Further aspects of the present invention become apparent to the one skilled in the art from the following detailed description of the invention and the examples.

BRIEF DESCRIPTION OF THE FIGURES

The FIG. 1 shows an X-ray powder diffractogram of the crystalline complex between the compound A and L-proline.
The FIG. 2 shows the determination of the melting point via DSC and of the weight loss via TG of the crystalline complex between the compound A and L-proline.

DETAILED DESCRIPTION OF THE INVENTION

Figure 1:
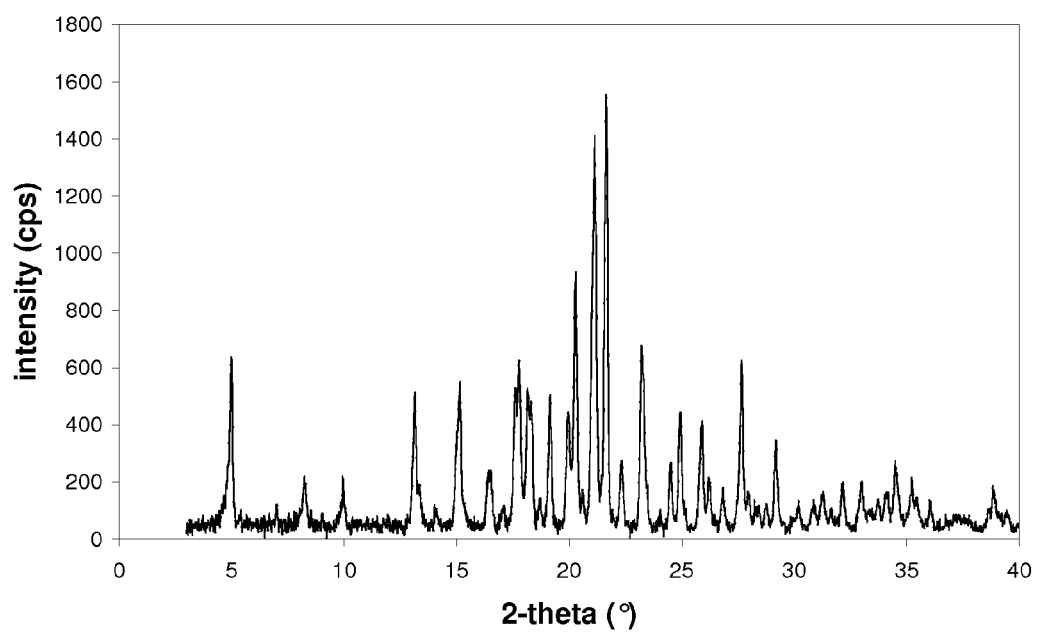

Surprisingly, it has been found that there exists a crystalline complex between a natural amino acid and the compound A. Such a complex fulfills important requirements mentioned hereinbefore. Accordingly the present invention relates to a crystalline complex between the compound A and one or more natural amino acids.

Preferably the natural amino acid is present in either its (D) or (L) enantiomeric form, most preferably as the (L) enantiomer.

Furthermore those crystalline complexes according to this invention are preferred which are formed between the compound A and one natural amino acid, most preferably between the compound A and the (L) enantiomer of a natural amino acid.

Preferred amino acids according to this invention are selected from the group consisting of phenylalanine and proline, in particular (L)-proline and (L)-phenylalanine.

According to a preferred embodiment the crystalline complex is characterized in that the natural amino acid is proline, in particular (L)-proline.

Preferably the molar ratio of the compound A and the natural amino acid is in the range from about 2:1 to about 1:3; more preferably from about 1.5:1 to about 1:1.5, even more preferably from about 1.2:1 to about 1:1.2, most preferably about 1:1. In the following it is referred to such an embodiment as "complex (1:1)" or "1:1 complex".

Therefore a preferred crystalline complex according to this invention is a complex (1:1) between the compound A and proline; in particular of the compound A and L-proline.

According to a preferred embodiment the crystalline complex, in the particular the 1:1 complex of the compound A with L-proline, is a hydrate.

Preferably the molar ratio of the crystalline complex and water is in the range from about 1:0 to 1:3; more preferably from about 1:0 to 1:2, even more preferably from about 1:0.5 to 1:1.5, most preferably about 1:0.8 to 1:1.2, in particular about 1:1.

The crystalline complex of the compound A with proline, in particular of the compound A with L-proline and water, may be identified and distinguished from other crystalline forms by means of their characteristic X-ray powder diffraction (XRPD) patterns.

Said crystalline complex is preferably characterized by an X-ray powder diffraction pattern that comprises peaks at 20.28, 21.14 and 21.64 degrees 2Θ (±0.1 degrees 2Θ), wherein said X-ray powder diffraction pattern is made using CuK$_{α1}$ radiation.

In particular said X-ray powder diffraction pattern comprises peaks at 4.99, 20.28, 21.14, 21.64 and 23.23 degrees 2Θ (±0.1 degrees 2Θ), wherein said X-ray powder diffraction pattern is made using CuK$_{α1}$ radiation.

More specifically said X-ray powder diffraction pattern comprises peaks at 4.99, 17.61, 17.77, 20.28, 21.14, 21.64, 23.23 and 27.66 degrees 2Θ (±0.1 degrees 2Θ), wherein said X-ray powder diffraction pattern is made using CuK$_{α1}$ radiation.

Even more specifically said X-ray powder diffraction pattern comprises peaks at 4.99, 15.12, 17.61, 17.77, 18.17, 20.28, 21.14, 21.64, 23.23 and 27.66 degrees 2Θ (±0.1 degrees 2Θ), wherein said X-ray powder diffraction pattern is made using CuK$_{α1}$ radiation.

Even more specifically, the crystalline complex of the compound A and L-proline is characterized by an X-ray powder diffraction pattern, made using CuK$_{α1}$ radiation, which comprises peaks at degrees 2Θ (±0.1 degrees 2Θ) as contained in Table 1.

TABLE 1

X-ray powder diffraction pattern of the crystalline complex of the compound A and L-proline (only peaks up to 30° in 2 Θ are listed):

| 2 Θ [°] | d-value [Å] | Intensity I/I$_0$ [%] |
|---|---|---|
| 4.99 | 17.68 | 39 |
| 7.01 | 12.61 | 6 |
| 8.25 | 10.70 | 11 |
| 9.95 | 8.88 | 12 |
| 13.15 | 6.73 | 30 |
| 13.33 | 6.64 | 10 |
| 14.08 | 6.28 | 4 |
| 15.12 | 5.85 | 32 |
| 16.40 | 5.40 | 12 |
| 16.49 | 5.37 | 13 |
| 17.11 | 5.18 | 6 |
| 17.61 | 5.03 | 32 |
| 17.77 | 4.99 | 35 |
| 18.17 | 4.88 | 32 |
| 18.32 | 4.84 | 28 |
| 18.72 | 4.74 | 8 |
| 19.16 | 4.63 | 30 |
| 19.96 | 4.45 | 26 |
| 20.28 | 4.37 | 56 |
| 20.60 | 4.31 | 7 |
| 21.14 | 4.20 | 84 |
| 21.64 | 4.10 | 100 |
| 22.33 | 3.98 | 15 |
| 23.23 | 3.83 | 41 |
| 24.06 | 3.70 | 4 |
| 24.51 | 3.63 | 15 |
| 24.93 | 3.57 | 26 |
| 25.89 | 3.44 | 23 |
| 26.21 | 3.40 | 11 |
| 26.84 | 3.32 | 8 |
| 27.66 | 3.22 | 38 |
| 27.96 | 3.19 | 9 |
| 28.26 | 3.16 | 5 |
| 28.44 | 3.14 | 6 |

TABLE 1-continued

X-ray powder diffraction pattern of the crystalline
complex of the compound A and L-proline (only peaks
up to 30° in 2 Θ are listed):

| 2 Θ [°] | d-value [Å] | Intensity $I/I_0$ [%] |
|---|---|---|
| 28.75 | 3.10 | 6 |
| 29.18 | 3.06 | 19 |

Even more specifically, said crystalline complex is characterized by an X-ray powder diffraction pattern, made using $CuK_{\alpha1}$ radiation, which comprises peaks at degrees 2Θ (±0.1 degrees 2Θ) as shown in FIG. 1.

Figure 2:
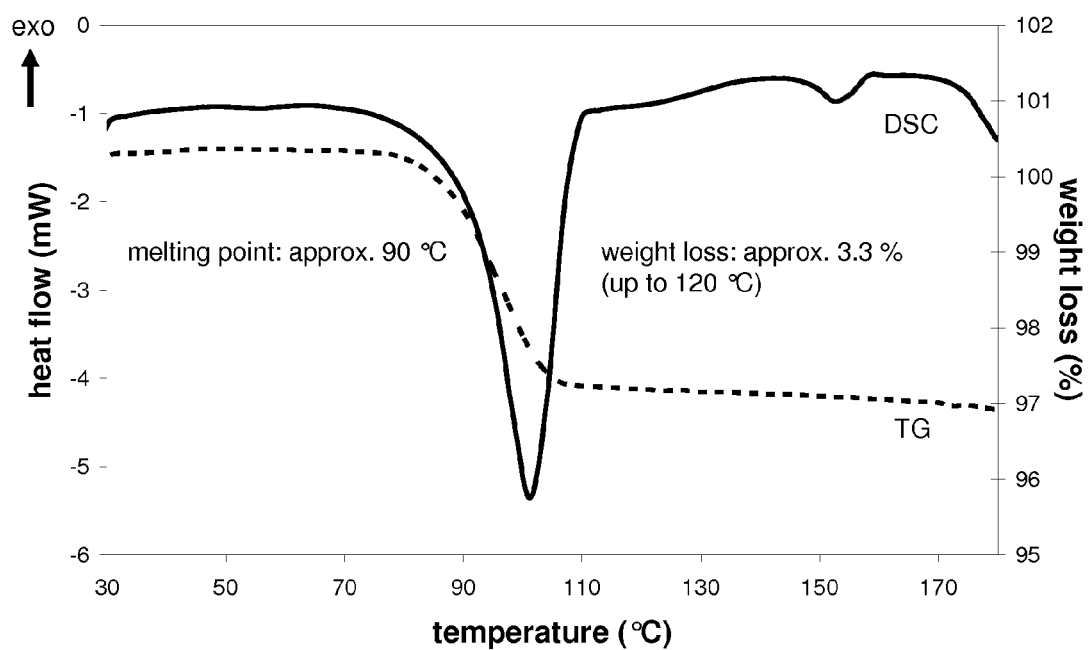

Furthermore said crystalline complex of the compound A with L-proline is characterized by a melting point of above 89° C., in particular in a range from about 89° C. to about 115° C., more preferably in a range from about 89° C. to about 110° C. (determined via DSC; evaluated as onset-temperature; heating rate 10K/min) It can be observed that this crystalline complex melts under dehydration. The obtained DSC curve is shown in FIG. 2.

Said crystalline complex of the compound A with L-proline shows a weight loss by thermal gravimetry (TG). The observed weight loss indicates that the crystalline form contains water which may be bound by adsorption and/or may be part of the crystalline lattice, i.e. the crystalline form may be present as a crystalline hydrate. The content of water in the crystalline form lies in the range from 0 to about 10 weight-%, in particular 0 to about 5 weight-%, even more preferably from about 1.5 to about 5 weight-%. The dotted line in FIG. 2 depicts a weight loss of between 2.8 and 3.8% of water. From the observed weight loss a stoichiometry close to a monohydrate can be estimated.

Said crystalline complex has advantageous physicochemical properties which are beneficial in the preparation of a pharmaceutical composition. In particular the crystalline complex has a high physical and chemical stability under various environmental conditions and during the production of a medicament. For example the crystals can be obtained in a shape and particle size which are particular suitable in a production method for solid pharmaceutical formulations. In addition the crystals show a high mechanical stability that allows grinding of the crystals. Furthermore the crystalline complex does not show a high tendency to absorb moisture and is chemically stable, i.e. the crystalline complex allows the production of a solid pharmaceutical formulation with a long shelf life. On the other hand the crystalline complex has a favorably high solubility over a wide pH-range which is advantageous in solid pharmaceutical formulations for oral administration.

The X-ray powder diffraction patterns are recorded, within the scope of the present invention, using a STOE-STADI P-diffractometer in transmission mode fitted with a location-sensitive detector (OED) and a Cu-anode as X-ray source ($CuK_{\alpha1}$ radiation, $\lambda$=1.54056 Å, 40 kV, 40 mA). In Table 1 the values "2Θ [°]" denote the angle of diffraction in degrees and the values "d [Å]" denote the specified distances in Å between the lattice planes. The intensity shown in FIG. 1 is given in units of cps (counts per second).

In order to allow for experimental error, the above described 2Θ values should be considered accurate to ±0.1 degrees 2Θ, in particular ±0.05 degrees 2Θ. That is to say, when assessing whether a given sample of crystals of the compound A is the crystalline form in accordance with the invention, a 2Θ value which is experimentally observed for the sample should be considered identical with a characteristic value described above if it falls within ±0.1 degrees 2Θ of the characteristic value, in particular if it falls within ±0.05 degrees 2Θ of the characteristic value.

The melting point is determined by DSC (Differential Scanning calorimetry) using a DSC 821 (Mettler Toledo). The weight loss is determined by thermal gravimetry (TG) using a TGA 851 (Mettler Toledo).

A further aspect of the present invention relates to a method for making the crystalline complex of the present invention as defined hereinbefore and hereinafter, said method comprising the following steps:

a) preparing a solution of the compound A and the one or more natural amino acids in a solvent or a mixture of solvents;

b) storing the solution to precipitate the crystalline complex out of solution;

c) removing the precipitate from the solution; and d) drying the precipitate optionally until any excess of said solvent or mixture of solvents has been removed.

According to step (a) a solution of the compound A and the one or more natural amino acids in a solvent or a mixture of solvents is prepared. Preferably the solution is saturated or at least nearly saturated or even supersaturated with respect to the crystalline complex. In the step (a) the compound (A) may be dissolved in a solution comprising the one or more natural amino acids or the one or more natural amino acids may be dissolved in a solution comprising the compounds A. According to an alternative procedure the compound A is dissolved in a solvent or mixture of solvents to yield a first solution and the one or more natural amino acids are dissolved in a solvent or mixture of solvents to yield a second solution. Thereafter said first solution and said second solution are combined to form the solution according to step (a).

Preferably the molar ratio of the natural amino acid and the compound A in the solution corresponds to the molar ratio of the natural amino acid and the compound A in the crystalline complex to be obtained. Therefore a preferred molar ratio is in the range from about 1:2 to 3:1; most preferably about 1:1.

Suitable solvents are preferably selected from the group consisting of $C_{1-4}$-alkanols, water, ethylacetate, acetonitrile, acetone, diethylether, tetrahydrofuran, and mixture of two or more of these solvents.

More preferred solvents are selected from the group consisting of methanol, ethanol, isopropanol, water and mixture of two or more of these solvents, in particular mixtures of one or more of said organic solvents with water.

Particularly preferred solvents are selected from the group consisting of ethanol, isopropanol, water and mixtures of ethanol and/or isopropanol with water.

In case a mixture of water and one or more $C_{1-4}$-alkanols, in particular of methanol, ethanol and/or isopropanol, most preferably of ethanol, is taken, a preferred volume ratio of water:the alkanol is in the range from about 99:1 to 1:99; more preferably from about 50:1 to 1:80; even more preferably from about 10:1 to 1:60.

Preferably the step (a) is carried out at about room temperature (about 20° C.) or at an elevated temperature up to about the boiling point of the solvent or mixture of solvents used.

According to a preferred embodiment the starting material of the compound A and/or of the one or more natural amino acids and/or of the solvent and mixtures of solvents contain an amount of $H_2O$ which is at least the quantity required to form a hydrate of the compound A; in particular at least 1 mol, preferably at least 1.5 mol of water per mol of compound A. Even more preferably the amount of water is at least 2 mol of water per mol of compound A. This means that either the compound A as starting material or the one or more natural amino acids or said solvent or mixture of solvents, or said compounds and/or solvents in combination contain an amount of $H_2O$ as specified above. For example if the starting material of the compound A or of the natural amino acid in step (a) does contain sufficient water as specified above, a water content of the solvent(s) is not mandatory.

In order to reduce the solubility of the crystalline complex according to this invention in the solution, in step (a) and/or in step (b) one or more antisolvents may be added, preferably during step (a) or at the beginning of step (b). Water is an example of a suitable antisolvent. The amount of antisolvent is preferably chosen to obtain a supersaturated or saturated solution with respect to the crystalline complex.

In step (b) the solution is stored for a time sufficient to obtain a precipitate, i.e. the crystalline complex. The temperature of the solution in step (b) is about the same as or lower than in step (a). During storage the temperature of the solution is preferably lowered, preferably to a temperature in the range of 20° C. to 0° C. or even lower. The step (b) can be carried out with or without stiffing. As known to the one skilled in the art by the period of time and the difference of temperature in step (b) the size, shape and quality of the obtained crystals can be controlled. Furthermore the crystallization may be induced by methods as known in the art, for example by mechanical means such as scratching or rubbing the contact surface of the reaction vessel for example with a glass rod. Optionally the (nearly) saturated or supersaturated solution may be inoculated with seed crystals.

In step (c) the solvent(s) can be removed from the precipitate by known methods as for example filtration, suction filtration, decantation or centrifugation.

In step (d) an excess of the solvent(s) is removed from the precipitate by methods known to the one skilled in the art as for example by reducing the partial pressure of the solvent(s), preferably in vacuum, and/or by heating above ca. 20° C., preferably in a temperature range below 100° C., even more preferably below 85° C.

The compound A may be synthesized by methods as specifically and/or generally described or cited in the international application WO 2007/128749. Furthermore the biological properties of the compound A may be investigated as it is described in the international application WO 2007/128749 which in their entirety are incorporated herein by reference.

The crystalline complex in accordance with the invention is preferably employed as drug active substance in substantially pure form, that is to say, essentially free of other crystalline forms of the compound A. Nevertheless, the invention also embraces the crystalline complex in admixture with another crystalline form or forms. Should the drug active substance be a mixture of crystalline forms, it is preferred that the substance comprises at least 50%-weight, even more preferably at least 90%-weight, most preferably at least 95%-weight of the crystalline complex as described herein.

In view of their ability to inhibit the SGLT activity, the crystalline complex according to the invention is suitable for the use in the treatment and/or preventive treatment of conditions or diseases which may be affected by the inhibition of the SGLT activity, particularly the SGLT-2 activity. The crystalline complex according to the invention is also suitable for the preparation of pharmaceutical compositions for the treatment and/or preventive treatment of conditions or diseases which may be affected by the inhibition of the SGLT activity, particularly the SGLT-2 activity. Therefore, the crystalline complex according to the invention is suitable for the use in the treatment of type 2 diabetes mellitus in humans.

The dosage required to achieve the corresponding activity for treatment or prevention usually depends on the patient, the nature and gravity of the illness or condition and the method and frequency of administration and is for the patient's doctor to decide. Expediently, the dosage may be from 1 to 100 mg by intravenous route, and 1 to 1000 mg by oral route, in each case administered 1 to 4 times a day. For this purpose, the pharmaceutical compositions according to this invention preferably comprise the crystalline complex according to the invention together with one or more inert conventional carriers and/or diluents. Such pharmaceutical compositions may be formulated as conventional galenic preparations such as plain or coated tablets, capsules, powders, suspensions or suppositories.

In the foregoing and following text, H atoms of hydroxyl groups are not explicitly shown in every case in structural formulae. The following example of synthesis serves to illustrate a method of preparing the compound A and its crystalline complex with L-proline as a natural amino acid. It is to be regarded only as a possible method described by way of example, without restricting the invention to its contents. The terms "room temperature" and "ambient temperature" are used interchangeably and denote temperatures of about 20° C. The following abbreviations are used:

DMF dimethylformamide

NMP N-methyl-2-pyrrolidone

THF tetrahydrofuran

PREPARATION OF THE STARTING COMPOUNDS

Example I

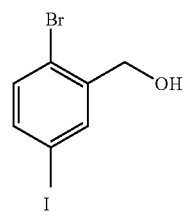

4-Bromo-3-hydroxymethyl-1-iodo-benzene

Oxalyl chloride (13.0 mL) is added to an ice-cold solution of 2-bromo-5-iodo-benzoic acid (49.5 g) in $CH_2Cl_2$ (200 mL). DMF (0.2 mL) is added and the solution is stirred at room temperature for 6 h. Then, the solution is concentrated under reduced pressure and the residue is dissolved in THF (100 mL). The resulting solution is cooled in an ice-bath and $LiBH_4$ (3.4 g) is added in portions. The cooling bath is removed and the mixture is stirred at room temperature for 1 h. The reaction mixture is diluted with THF and treated with 0.1M hydrochloric acid. Then, the organic layer is separated and the aqueous layer is extracted with ethyl acetate. The combined organic layers are dried ($Na_2SO_4$) and the solvent is evaporated under reduced pressure to give the crude product.

Yield: 47.0 g (99% of theory)

Example II

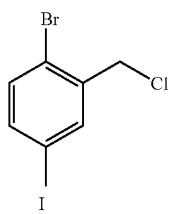

4-Bromo-3-chloromethyl-1-iodo-benzene

Thionyl chloride (13 mL) is added to a suspension of 4-bromo-3-hydroxymethyl-1-iodo-benzene (47.0 g) in dichloromethane (100 mL) containing DMF (0.1 mL). The mixture is stirred at ambient temperature for 3 h. Then, the solvent and the excess reagent is removed under reduced pressure. The residue is triturated with methanol and dried.

Yield: 41.0 g (82% of theory)

Example III

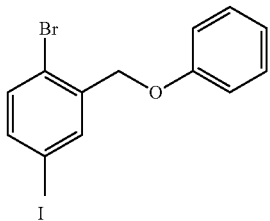 [SMILES: Brc1ccc(I)cc1COc1ccccc1]

4-Bromo-1-iodo-3-phenoxymethyl-benzene

Phenol (13 g) dissolved in 4 M KOH solution (60 mL) is added to 4-bromo-3-chloromethyl-1-iodo-benzene (41.0 g) dissolved in acetone (50 mL). NaI (0.5 g) is added and the resulting mixture is stirred at 50° C. overnight. Then, water is added and the resulting mixture is extracted with ethyl acetate. The combined extracts are dried ($Na_2SO_4$) and the solvent is evaporated under reduced pressure. The residue is purified by chromatography on silica gel (cyclohexane/ethyl acetate 19:1).

Yield: 38.0 g (79% of theory)

Example IV

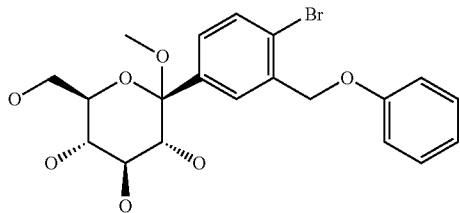 [SMILES: CO[C@@]1(c2ccc(Br)c(COc3ccccc3)c2)O[C@H](CO)[C@@H](O)[C@H](O)[C@H]1O]

1-Bromo-4-(1-methoxy-D-glucopyranos-1-yl)-2-(phenoxymethyl)-benzene

A 2 M solution of iPrMgCl in THF (11 mL) is added to dry LiCl (0.47 g) suspended in THF (11 mL). The mixture is stirred at room temperature until all the LiCl is dissolved. This solution is added dropwise to a solution of 4-bromo-1-iodo-3-phenoxymethyl-benzene (8.0 g) in tetrahydrofuran (40 mL) cooled to −60° C. under argon atmosphere. The solution is warmed to −40° C. and then 2,3,4,6-tetrakis-O-(trimethylsilyl)-D-glucopyranone (10.7 g, 90% pure) in tetrahydrofuran (5 mL) is added. The resulting solution is warmed to −5° C. in the cooling bath and stirred for another 30 min at this temperature. Aqueous $NH_4Cl$ solution is added and the resultant mixture is extracted with ethyl acetate. The combined organic extracts are dried over sodium sulfate and the solvent is removed under reduced pressure. The residue is dissolved in methanol (80 mL) and treated with methanesulfonic acid (0.6 mL) to produce the more stable anomer solely. After stirring the reaction solution at 35-40° C. overnight, the solution is neutralized with solid $NaHCO_3$ and the methanol is removed under reduced pressure. The remainder is diluted with aqueous $NaHCO_3$ solution and the resulting mixture is extracted with ethyl acetate. The combined extracts are dried over sodium sulfate and the solvent is evaporated to yield the crude product that is submitted to reduction without further purification.

Yield: 7.8 g (93% of theory)

Example V

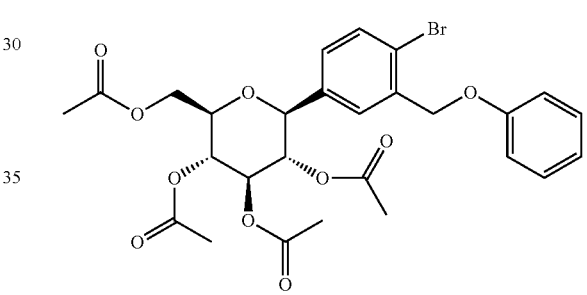

1-Bromo-4-(2,3,4,6-tetra-O-acetyl-D-glucopyranos-1-yl)-2-(phenoxymethyl)-benzene Boron trifluoride diethyletherate (4.9 mL) is added to a solution of 1-bromo-4-(1-methoxy-D-glucopyranos-1-yl)-2-(phenoxymethyl)-benzene (8.7 g) and triethylsilane (9.1 mL) in dichloromethane (35 mL) and acetonitrile (50 mL) cooled to −20° C. at such a rate that the temperature maintains below −10° C. The resultant solution is warmed to 0° C. over a period of 1.5 h and then treated with aqueous sodium hydrogen carbonate solution. The resulting mixture is stirred for 0.5 h, the organic solvent is removed and the residue is extracted with ethyl acetate. The combined organic layers are dried over sodium sulfate and the solvent is removed. The residue is taken up in dichloromethane (50 mL) and pyridine (9.4 mL), acetic anhydride (9.3 mL) and 4-dimethylaminopyridine (0.5 g) are added in succession to the solution. The solution is stirred for 1.5 h at ambient temperature and then diluted with dichloromethane. This solution is washed twice with 1M hydrochloric acid and dried over sodium sulfate. After the solvent is removed, the residue is recrystallized from ethanol to furnish the product as a colorless solid.

Yield: 6.78 g (60% of theory)

Mass spectrum ($ES^+$): m/z=610/612 (Br) $[M+NH_4]^+$

Example VI

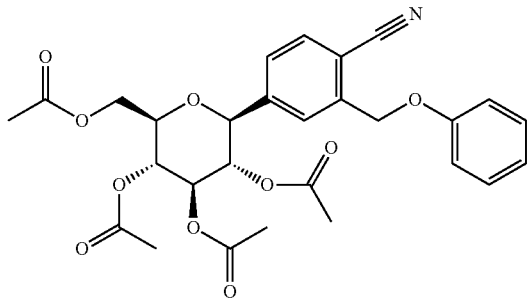 [SMILES: CC(=O)OC[C@H]1O[C@@H](c2ccc(C#N)c(COc3ccccc3)c2)[C@H](OC(C)=O)[C@@H](OC(C)=O)[C@@H]1OC(C)=O]

2-(Phenoxymethyl)-4-(2,3,4,6-tetra-O-acetyl-D-glucopyranos-1-yl)-benzonitrile

A flask charged with zinc cyanide (1.0 g), zinc (30 mg), Pd$_2$(dibenzylideneacetone)$_3$*CHCl$_3$ (141 mg) and tri-tert-butylphosphonium tetrafluoroborate (111 mg) is flushed with argon. Then a solution of 1-bromo-4-(2,3,4,6-tetra-O-acetyl-D-glucopyranos-1-yl)-2-(phenoxymethyl)-benzene (5.4 g) in NMP (12 mL) is added and the resulting mixture is stirred at room temperature for 18 h. After dilution with ethyl acetate, the mixture is filtered and the filtrate is washed with aqueous sodium hydrogen carbonate solution. The organic phase is dried (sodium sulfate) and the solvent is removed. The residue is recrystallized from ethanol.

Yield: 4.10 g (84% of theory)

Mass spectrum (ES$^+$): m/z=557 [M+NH$_4$]$^+$

Alternatively, the compound described above is synthesized starting from 1-bromo-4-(2,3,4,6-tetra-O-acetyl-D-glucopyranos-1-yl)-2-(phenoxymethyl)-benzene using copper(I) cyanide (2 equivalents) in NMP at 210° C.

Example VII

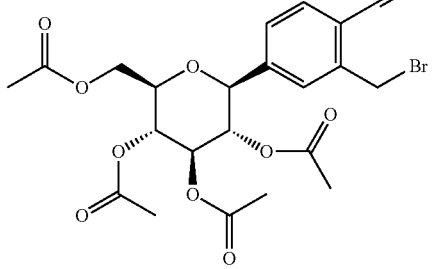

2-Bromomethyl-4-(2,3,4,6-tetra-O-acetyl-D-glucopyranos-1-yl)-benzonitrile

A 33% solution of hydrobromic acid in acetic acid (15 mL) is added to a solution of 2-phenyloxymethyl-4-(2,3,4,6-tetra-O-acetyl-D-glucopyranos-1-yl)-benzonitrile (0.71 g) and acetic anhydride (0.12 mL) in acetic acid (10 ml). The resulting solution is stirred at 55° C. for 6 h and then cooled in an ice-bath. The reaction mixture is neutralized with chilled aqueous potassium carbonate solution, and the resultant mixture is extracted with ethyl acetate. The combined organic extracts are dried over sodium sulfate and the solvent is removed under reduced pressure. The residue is taken up in ethyl acetate/cyclohexane (1:5), and the precipitate is separated by filtration and dried at 50° C. to give the pure product.

Yield: 0.52 g (75% of theory)

Mass spectrum (ES$^+$): m/z=543/545 (Br) [M+NH$_4$]$^+$

Example VIII

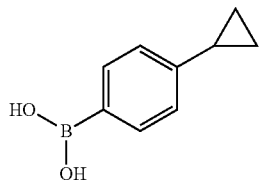 [SMILES: OB(O)c1ccc(C2CC2)cc1]

4-Cyclopropyl-phenylboronic acid 2.5 M solution of nButyllithium in hexane (14.5 mL) is added dropwise to 1-bromo-4-cyclopropyl-benzene (5.92 g) dissolved in THF (14 mL) and toluene (50 mL) and chilled to −70° C. The resultant solution is stirred at −70° C. for 30 min before triisopropyl borate (8.5 mL) is added. The solution is warmed to −20° C. and then treated with 4 M aqueous hydrochloric acid (15.5 mL). The reaction mixture is further warmed to room temperature and then the organic phase is separated. The aqueous phase is extracted with ethyl acetate and the combined organic phases are dried (sodium sulfate). The solvent is evaporated and the residue is washed with a mixture of ether and cyclohexane to give the product as a colorless solid.

Yield: 2.92 g (60% of theory)

Mass spectrum (ESI$^-$): m/z=207 (Cl) [M+HCOO]$^-$

Preparation of the Compound A

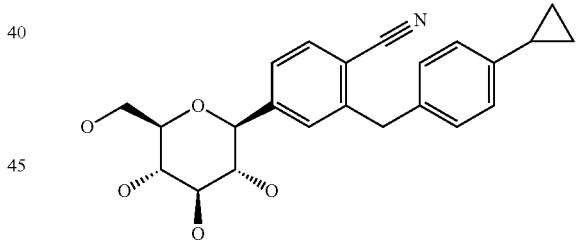

1-Cyano-2-(4-cyclopropyl-benzyl)-4-(β-D-glucopyranos-1-yl)-benzene

An Ar filled flask is charged with 2-bromomethyl-4-(2,3,4,6-tetra-O-acetyl-D-glucopyranos-1-yl)-benzonitrile (1.60 g), 4-cyclopropyl-phenylboronic acid (1.0 g), potassium carbonate (1.85 g) and a degassed 3:1 mixture of acetone and water (22 mL). The mixture is stirred at room temperature for 5 min, before it is cooled in an ice-bath. Then palladium dichloride (30 mg) is added and the reaction mixture is stirred for 16 h at ambient temperature. The mixture is then diluted with brine and extracted with ethyl acetate. The combined extracts are dried over sodium sulfate and the solvent is removed under reduced pressure. The residue is dissolved in methanol (20 mL) and treated with 4 M aqueous potassium hydroxide solution (4 mL). The resulting solution is stirred at ambient temperature for 1 h and then neutralized with 1M hydrochloric acid. The methanol is evaporated, and the residue is diluted with brine and extracted with ethyl acetate. The organic extracts collected are dried over sodium sulfate, and the solvent is removed. The residue is chromatographed on silica gel (dichloromethane/methanol 1:0->8:1).

Yield: 0.91 g (76% of theory)

Mass spectrum (ES$^+$): m/z=413 [M+NH$_4$]$^+$

Preparation of the Crystalline Complex (1:1) with L-Proline

L-proline (0.34 g) dissolved in 2.1 mL of a mixture of ethanol and water (volume ratio 10:1) is added to a solution of 1-cyano-2-(4-cyclopropyl-benzyl)-4-(β-D-glucopyranos-1-yl)-benzene (1.17 g, obtained as described above) dissolved in 2 mL ethanol. The resulting solution is allowed to stand at ambient temperature. After about 16 h the crystalline complex is isolated as white crystals by filtration. If necessary the crystallization may be initiated by scratching with a glass rod or metal spatula for example or by inoculating with seed crystals. Residual solvent is removed by storing the crystals at slightly elevated temperature (30 to 50° C.) under vacuum for about 4 h to yield 1.27 g of the crystalline 1:1 complex of L-proline and 1-cyano-2-(4-cyclopropyl-benzyl)-4-(β-D-glucopyranos-1-yl)-benzene.

Several batches of the crystalline complex according to the above preparation are obtained. The X-ray powder diffraction patterns coincide. The melting points are determined via DSC and evaluated as onset-temperature. Examples of melting points are approximately 89° C., 90° C., 92° C., 101° C. and 110° C. The X-ray powder diffraction pattern as contained in Table 1 and as depicted in FIG. 1 and the DSC and TG diagram in FIG. 2 correspond to a batch with a melting point of approximately 90° C.

What is claimed is:

1. Crystalline complex between 1-cyano-2-(4-cyclopropyl-benzyl)-4-(β-D-glucopyranos-1-yl)-benzene and one or more natural amino acids.

2. Crystalline complex according to claim 1, wherein the natural amino acid is proline.

3. Crystalline complex according to claim 2, wherein it is a complex of 1-cyano-2-(4-cyclopropyl-benzyl)-4-(β-D-glucopyranos-1-yl)-benzene and proline with a molar ratio in the range from about 2:1 to about 1:3.

4. Crystalline complex according to claim 2 wherein the content of water is in the range from about 0 to 3 mol per mol of 1-cyano-2-(4-cyclopropyl-benzyl)-4-(β-D-glucopyranos-1-yl)-benzene.

5. Crystalline complex according to claim 2, wherein the crystalline complex is characterized by an X-ray powder diffraction pattern made using CuK$_{α1}$ radiation that comprises peaks at 20.28, 21.14 and 21.64 degrees 2Θ(±0.1 degrees 2Θ).

6. Crystalline complex according to claim 5, wherein the X-ray powder diffraction pattern made using CuK$_{α1}$ radiation further comprises peaks at 4.99 and 23.23 degrees 2Θ(±0.1 degrees 2Θ).

7. Crystalline complex according to claim 5, wherein the X-ray powder diffraction pattern made using CuK$_{α1}$ radiation further comprises peaks at 17.61, 17.77 and 27.66 degrees 2Θ(±0.1 degrees 2Θ).

8. Crystalline complex according to claim 1 wherein at least 50% of said complex is present as a crystalline complex in accordance with claim 5.

9. A pharmaceutical composition comprising one or more crystalline complexes in accordance with claim 1.

10. A medicament comprising the crystalline complex of claim 1.

11. A method for treatment of type 2 diabetes mellitus the crystalline complex of claim 1.

12. A method for inhibition of sodium dependent glucose cotransporter SGLT2 in a subject, the method comprising administering to the subject the crystalline complex of claim 1.

13. A method for making the crystalline complex in accordance with claim 1, said method comprising the following steps:
   a) preparing a solution of 1-cyano-2-(4-cyclopropyl-benzyl)-4-(β-D-glucopyranos-1-yl)-benzene and the one or more natural amino acids in a solvent or a mixture of solvents;
   b) storing the solution to precipitate the crystalline complex out of solution;
   c) removing the precipitate from the solution; and
   d) drying the precipitate optionally until any excess of said solvent or mixture of solvents has been removed.

* * * * *